US008848937B2

(12) United States Patent
Inoue et al.

(10) Patent No.: US 8,848,937 B2
(45) Date of Patent: Sep. 30, 2014

(54) ACTIVE NOISE CONTROL APPARATUS

(71) Applicant: Honda Motor Co., Ltd., Tokyo (JP)

(72) Inventors: Toshio Inoue, Tochigi-ken (JP); Kosuke Sakamoto, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 13/894,149

(22) Filed: May 14, 2013

(65) Prior Publication Data

US 2013/0315409 A1 Nov. 28, 2013

(30) Foreign Application Priority Data

May 22, 2012 (JP) ................................ 2012-116321

(51) Int. Cl.

| | |
|---|---|
| ***A61F 11/06*** | (2006.01) |
| ***G10K 11/16*** | (2006.01) |
| ***G10K 11/178*** | (2006.01) |

(52) U.S. Cl.

CPC .......... *G10K 11/16* (2013.01); *G10K 2210/121* (2013.01); *G10K 2210/511* (2013.01); *G10K 2210/3039* (2013.01); *G10K 2210/12821* (2013.01); *G10K 2210/503* (2013.01); *G10K 11/1784* (2013.01)

USPC ........................................................ 381/71.1

(58) Field of Classification Search

CPC ............. G10K 11/1788; G10K 11/178; G10L 21/0208; G10L 2021/02165; H04R 5/005

USPC ....................... 381/86, 94.1–94.4, 71.1–71.5, 381/71.11–71.14

See application file for complete search history.

(56) References Cited

U.S. PATENT DOCUMENTS

| | | | | |
|---|---|---|---|---|
| 5,627,896 | A * | 5/1997 | Southward et al. | ........ 381/71.11 |
| 5,710,822 | A * | 1/1998 | Steenhagen et al. | ....... 381/71.12 |
| 5,809,152 | A * | 9/1998 | Nakamura et al. | ........... 381/71.8 |
| 2009/0060217 | A1 | 3/2009 | Sakamoto et al. | |
| 2011/0123042 | A1 | 5/2011 | Sakamoto et al. | |

FOREIGN PATENT DOCUMENTS

| | | | | |
|---|---|---|---|---|
| JP | 03-203497 | A | 9/1991 | |
| JP | 7-104767 | A | 4/1995 | |
| JP | 10-214119 | A | 8/1998 | |
| JP | 2009-57018 | A | 3/2009 | |
| JP | 2009-292201 | * | 12/2009 | ........... G10K 11/178 |
| JP | 2009-292201 | A | 12/2009 | |
| JP | 2010-202136 | A | 9/2010 | |

OTHER PUBLICATIONS

European Search Report issued in Application No. 13167833.6, dated Jan. 23, 2014, 7 pages.

Office Action dated Jun. 3, 2014 issued over the corresponding Japanese Patent Application 2012-116321 with the English translation of pertinent portion.

* cited by examiner

*Primary Examiner* — Lun-See Lao

(74) *Attorney, Agent, or Firm* — Carrier Blackman & Associates, P.C.; Joseph P. Carrier; William D. Blackman

(57) ABSTRACT

An active noise control apparatus includes a first active noise controller for generating a first canceling signal for a first noise type, a second active noise controller for generating a second canceling signal for a second noise type that is different from the first noise type, a mixer for mixing the first canceling signal and the second canceling signal into a mixed canceling signal, a canceling sound output unit for outputting a canceling sound based on the mixed canceling signal, and an amplitude suppressor for suppressing the amplitude of the second canceling signal depending on the amplitude of the first canceling signal.

7 Claims, 9 Drawing Sheets

FIG. 2

40

| PRIORITY LEVEL | ACTIVE NOISE CONTROLLER | CANCELING SIGNAL | FILTER COEFFICIENT |
|---|---|---|---|
| 1 | 11 | Sc1 (ROAD NOISE 1) | W1 |
| 2 | 13 | Sc3 (ROAD NOISE 2) | W3 |
| 3 | 12 | Sc2 (MUFFLED ENGINE SOUND 1) | W2 |
| 4 | 14 | Sc4 (MUFFLED PROPELLER SHAFT SOUND 2) | W4 |

ACTIVE NOISE CONTROL APPARATUS

CROSS-REFERENCE TO RELATED APPLICATION

This application is based upon and claims the benefit of priority from Japanese Patent Application No. 2012-116321 filed on May 22, 2012, the contents of which are incorporated herein by reference.

BACKGROUND OF THE INVENTION

1. Field of the Invention

The present invention relates to an active noise control apparatus for controlling the noise in the passenger compartment of a vehicle, and more particularly to an active noise control apparatus having a mixer for mixing canceling signals output from a plurality of active noise controllers into a mixed canceling signal.

2. Description of the Related Art

Noise types that have heretofore been known as occurring in the passenger compartments of vehicles include a muffled sound caused by the combustion of fuel by the engine (hereinafter referred to as "muffled engine sound"), a muffled sound caused by unbalanced rotation of a drive-system rotational member such as a propeller shaft while the vehicle is traveling (hereinafter referred to as "muffled propeller shaft sound"), and a noise transmitted from the road through road wheels and suspensions (hereinafter referred to as "road noise").

In order to reduce these noises, a canceling signal for canceling the muffled engine sound and a canceling signal for canceling the road noise are generated by respective active noise controllers (see Japanese Laid-Open Patent Publication No. 07-104767, Japanese Laid-Open Patent Publication No. 10-214119, Japanese Laid-Open Patent Publication No. 2009-057018, and Japanese Laid-Open Patent Publication No. 2009-292201).

In view of cost, space, and other factors, a speaker used as the music sound output unit of a music sound device in the passenger compartment is shared as a canceling sound output unit.

The canceling signal for canceling the muffled engine sound and the canceling signal for canceling the road noise are mixed or added into a mixed canceling signal by a mixer, and the mixed canceling signal is supplied to the speaker, which outputs a canceling sound.

SUMMARY OF THE INVENTION

The mixer has an output range, i.e., a dynamic range, which is limited to n bits, for example. According to the related art, the output range of the mixer is divided into a plurality of equal subranges depending on the number of canceling signals used, e.g., "m", and the subranges are assigned to the respective canceling signals and used in operation.

Active noise control apparatus according to the related art which operate in the manner described above are problematic in that if the amplitude or magnitude of a certain canceling signal becomes too large, then even though the total output range of the mixer is wide enough, the certain canceling signal tends to be clipped in the subrange to which it is assigned, resulting in a reduced noise canceling capability. In particular, the road noise is liable to change greatly in magnitude on different roads, and hence it is difficult to establish a properly predicted subrange for the road noise. Consequently, the active noise control apparatus according to the related art have room for improvement with respect to the cancelation of the road noise.

It is an object of the present invention to provide an active noise control apparatus which is capable of outputting an optimum canceling sound depending on how a vehicle that incorporates the active noise control apparatus travels, by optimizing the use of the output range of a mixer.

Noise types that can be handled by an active noise control apparatus according to the present invention include at least two noise types among a muffled engine sound, a muffled propeller shaft sound, a road noise, a wind noise that is generated by air streams that flow along the surfaces of a vehicle body, and an acceleration sound (pseudo-acceleration sound) generated and output into a passenger compartment depending on the rotational speed of an engine rotational speed.

According to the present invention, there is provided an active noise control apparatus comprising a first active noise controller for generating a first canceling signal for a first noise type, a second active noise controller for generating a second canceling signal for a second noise type that is different from the first noise type, a mixer for mixing the first canceling signal and the second canceling signal into a mixed canceling signal, a canceling sound output unit for outputting a canceling sound based on the mixed canceling signal, and an amplitude suppressor for suppressing an amplitude of the second canceling signal depending on an amplitude of the first canceling signal.

According to the present invention, since the active noise control apparatus has the amplitude suppressor that suppresses the amplitude of the second canceling signal which is input to the mixer depending on the amplitude of the first canceling signal which is input to the mixer, the active noise control apparatus is capable of outputting an optimum canceling sound depending on how a vehicle that incorporates the active noise control apparatus travels, by optimizing the use of the output range of the mixer.

If a sum of the amplitude of the first canceling signal and the amplitude of the second canceling signal is greater than a maximum output amplitude allowed by the mixer, the amplitude suppressor sets the amplitude of the second canceling signal to a difference which is produced when the amplitude of the first canceling signal is subtracted from the maximum output amplitude allowed by the mixer, preventing the amplitude of the first canceling signal from being clipped as much as possible.

If the sum of the amplitude of the first canceling signal and the amplitude of the second canceling signal is greater than a maximum output amplitude allowed by the mixer, the amplitude suppressor sets the amplitude of the second canceling signal to zero, also preventing the amplitude of the first canceling signal from being clipped as much as possible.

The first active noise controller and the second active noise controller include adaptive notch filters, respectively, and the amplitude suppressor calculates the amplitude of the first canceling signal and the amplitude of the second canceling signal based on respective filter coefficients of the adaptive notch filters. Therefore, the amplitude of the first canceling signal and the amplitude of the second canceling signal can be calculated simply.

When the first noise type represents a road noise, even if the amplitude of the first canceling signal cannot be predicted beforehand, the desired first canceling signal for generating a canceling sound for canceling the road noise is prevented from being clipped, and the active noise control apparatus is capable of outputting an optimum canceling sound depending on how a vehicle that incorporates the active noise control apparatus travels, by optimizing the use of the output range of the mixer.

According to the present invention, there is also provided an active noise control apparatus comprising a plurality of active noise controllers for generating a plurality of canceling signals respectively for a plurality of noise types, a mixer for mixing the canceling signals into a mixed canceling signal, a canceling sound output unit for outputting a canceling sound based on the mixed canceling signal, the noise types being in accordance with a noise reduction priority sequence preset therefor, and an amplitude suppressor for suppressing an amplitude of at least one of the canceling signals depending on the noise reduction priority sequence.

Since the amplitude of at least one of the canceling signals, which cancels the noise type whose priority level is lower, is suppressed by the amplitude suppressor, the amplitude of the canceling signal for canceling the noise type whose priority level is higher is prevented from being suppressed accordingly.

According to the present invention, inasmuch as the active noise control apparatus has the amplitude suppressor that suppresses the amplitude of the second canceling signal which is input to the mixer depending on the amplitude of the first canceling signal which is input to the mixer, the active noise control apparatus is capable of outputting an optimum canceling sound depending on how a vehicle that incorporates the active noise control apparatus travels, by optimizing the use of the output range of the mixer.

According to the present invention, furthermore, as the amplitude of at least one of the canceling signals, which cancels the noise type whose priority level is lower, is suppressed by the amplitude suppressor, the amplitude of the canceling signal for canceling the noise type whose priority level is higher is prevented from being suppressed accordingly.

The noise reduction priority sequence has a succession of priority levels set respectively to a road noise which is caused by resonance of suspensions and has its magnitude that varies depending on conditions of a road, a drumming noise caused by resonance of a sound field in a passenger compartment, a muffled engine sound corresponding to a rotational frequency of an engine crankshaft, and a muffled propeller shaft sound corresponding to a rotational frequency of a propeller shaft.

The amplitude suppressor may update a remaining output range of the mixer each time one of the amplitudes of the canceling signals generated respectively by the active noise controllers is assigned to the output range of the mixer in a descending order of the noise types according to the noise reduction priority sequence, and performs a forgetting process for fading out the amplitude of one of the canceling signals for the noise types which cannot be assigned within the remaining output range of the mixer.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 2 is a noise reduction priority sequence table for first through fourth active noise controllers of the active noise control apparatus according to the embodiment;

DESCRIPTION OF THE PREFERRED EMBODIMENTS

Active noise control apparatus according to preferred embodiments of the present invention will be described below with reference to the accompanying drawings.

Figure 1:
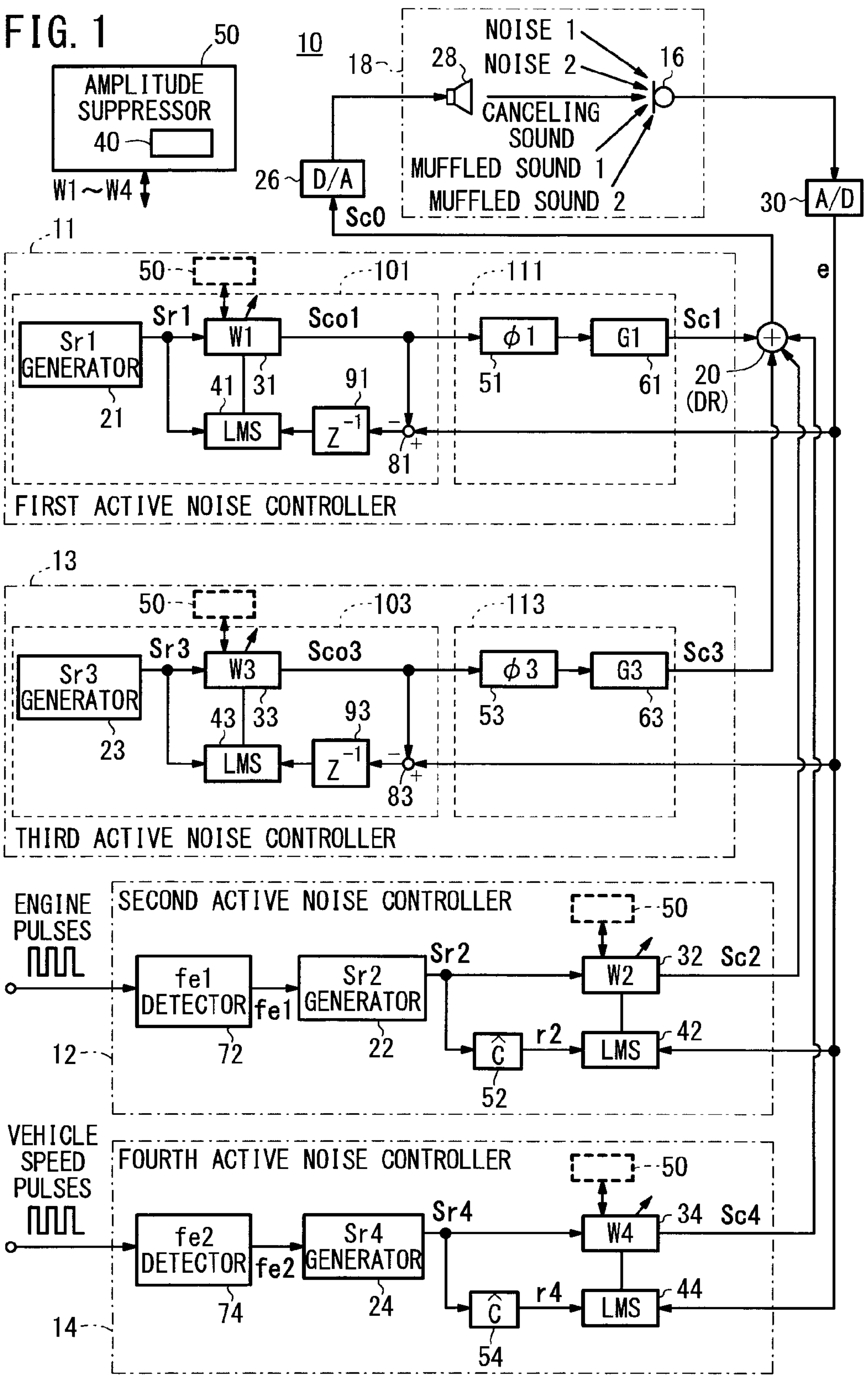
FIG. 1 is a block diagram showing a configuration of an active noise control apparatus according to an embodiment of the present invention.

FIG. 1 shows in block form an active noise control apparatus 10 according to an embodiment of the present invention.

As shown in FIG. 1, the active noise control apparatus 10, which is incorporated in a vehicle, basically includes a first active noise controller 11 for generating a first canceling signal Sc1 to generate a canceling sound for canceling a road noise 1 having a frequency f1, a second active noise controller 12 for generating a second canceling signal Sc2 to generate a canceling sound for canceling a muffled engine sound 1, a third active noise controller 13 for generating a third canceling signal Sc3 to generate a canceling sound for canceling a road noise 2 having a frequency f2 which is different from the frequency f1, a fourth active noise controller 14 for generating a fourth canceling signal Sc4 to generate a canceling sound for canceling a muffled propeller shaft sound 2, and an amplitude suppressor 50 serving as an amplitude controller for controlling respective amplitudes A1, A2, A3, A4 of the first, second, third, and fourth canceling signals Sc1, Sc2, Sc3, Sc4 when necessary. The active noise control apparatus 10 performs a control process for silencing the road noises 1, 2 (indicated as NOISE 1, NOISE 2 in FIG. 1), the muffled engine sound 1 (indicated as MUFFLED SOUND 1 in FIG. 1), and the muffled propeller shaft sound 2 (indicated as MUFFLED SOUND 2 in FIG. 1) in a cooperative fashion.

The first, second, third, and fourth active noise controllers 11, 12, 13, 14 and the amplitude suppressor 50 are implemented by a computer or a plurality of computers, whose CPU or CPUs read and execute programs stored in a memory or memories such as ROMs in response to various input signals applied thereto, thereby acting as a function performer (also called "function performing means") for performing various functions.

The first, second, third, and fourth canceling signals Sc1, Sc2, Sc3, Sc4 are mixed or added into a mixed canceling signal Sc0 (Sc0=Sc1+Sc2+Sc3+Sc4) by a mixer (adder) 20 having an output range DR. Based on the mixed canceling signal Sc0, a D/A converter 26 supplies an output signal to a speaker (canceling sound output unit) 28 disposed in a passenger compartment space 18. In response to the output signal from the D/A converter 26, the speaker 28 outputs or radiates the canceling sounds for canceling the road noises 1, 2, the muffled engine sound 1, and the muffled propeller shaft sound 2.

It is to be noted that if an amplitude level which is twice (full amplitude) the amplitude (half amplitude) of the mixed canceling signal Sc0 exceeds the output range DR of the mixer 20, then the mixed canceling signal Sc0 is clipped by the mixer 20. In other words, the mixer 20 has an allowable maximum output amplitude that is one-half of the output range DR.

A microphone (error signal detector) 16 for detecting a remaining noise generated by the interference between the muffled engine sound 1, the muffled propeller shaft sound 2, and the road noises 1, 2 and the canceling sounds therefor is disposed at an evaluating point (evaluating position, hearing point) in the passenger compartment space 18.

The microphone 16 outputs an error signal e which is converted by an A/D converter 30 into a digital error signal e. The digital error signal e is supplied as an input signal to the first, second, third, and fourth active noise controllers 11, 12, 13, 14.

The first and third active noise controllers 11, 13 for silencing the road noises 1, 2 have respective first and third adaptive notch filters 101, 103 functioning as bandpass filters and respective simulative transfer characteristics sections 111, 113.

The first adaptive notch filter 101 of the first active noise controller 11 includes a first base signal generator (Sr1 generator) 21 for generating a first base signal Sr1 {cosine signal cos(2πfd1*t*) and sine signal sin(2πfd1*t*)} in synchronism with the frequency fd1 [Hz] of the road noise 1, which is about a frequency of 120 [Hz], for example, inherent in the type of the vehicle, a first adaptive filter 31 for generating, from the first base signal Sr1, an original first canceling signal Sco1 that is substantially equal in amplitude and phase to a component, which has the frequency fd1 of the road noise 1, of the error signal e at a subtrahend terminal of a subtractor 81, and a filter coefficient updater (algorithm processor) 41.

The filter coefficient updater 41 is supplied with the first base signal Sr1 and a signal (e−Sco1) that is produced by subtracting the original first canceling signal Sco1 from the error signal e with the subtractor 81 and delaying the difference with a 1-sample delay element 91. The filter coefficient updater 41 updates a filter coefficient W1 (real part+i imaginary part=Rw1+iIw1) of the first adaptive filter 31 of the first adaptive notch filter 101 based on an adaptive control algorithm for minimizing the signal (e−Sco1), e.g., an LMS (Least Mean Square) algorithm which is one type of steepest descent method.

The road noise 1 having the frequency fd1 is caused by the resonance of suspensions, and has its magnitude which varies greatly depending on the conditions of the road.

The simulative transfer characteristics section 111 includes a phase shifter 51 and a gain setter (gain adjuster) 61. The phase shifter 51 is preset to a phase shift for shifting the phase of the original first canceling signal Sco1 having the frequency fd1 which is input to the phase shifter 51 so that the original first canceling signal Sco1 will be in opposite phase with the road noise 1 at the position of the microphone 16. The gain setter 61 is set to a gain G1 for changing the amplitude of the original first canceling signal Sco1 shifted in phase by the phase shifter 51 so that it will become substantially equal to the amplitude of the road noise 1 at the position of the microphone 16.

The third adaptive notch filter 103 of the third active noise controller 13 includes a third base signal generator (Sr3 generator) 23 for generating a third base signal Sr3 {cosine signal cos(2πfd2*t*) and sine signal sin(2πfd2*t*)} in synchronism with the frequency fd2 [Hz] of the road noise 2, which is about a frequency of 40 [Hz], for example, inherent in the type of the vehicle, a third adaptive filter 33 for generating, from the third base signal Sr3, an original third canceling signal Sco3 that is substantially equal in amplitude and phase to a component, which has the frequency fd2 of the road noise 2, of the error signal e at a subtrahend terminal of a subtractor 83, and a filter coefficient updater (algorithm processor) 43.

The filter coefficient updater 43 is supplied with the third base signal Sr3 and a signal (e−Sco3) that is produced by subtracting the original third canceling signal Sco3 from the error signal e with the subtractor 83 and delaying the difference with a 1-sample delay element 93. The filter coefficient updater 43 updates a filter coefficient W3 (real part+i imaginary part=Rw3+iIw3) of the third adaptive filter 33 of the third adaptive notch filter 103 based on an adaptive control algorithm for minimizing the signal (e−Sco3), e.g., an LMS algorithm which is one type of steepest descent method.

The road noise 2 having the frequency fd2 is a so-called drumming noise caused by the resonance etc. of the sound field in the passenger compartment, and has its magnitude which does not vary as greatly as the road noise 1.

The simulative transfer characteristics section 113 includes a phase shifter 53 and a gain setter (gain adjuster) 63. The phase shifter 53 is preset to a phase shift for shifting the phase of the original third canceling signal Sco3 having the frequency fd2 which is input to the phase shifter 53 so that the original third canceling signal Sco3 will be in opposite phase with the road noise 2 at the position of the microphone 16. The gain setter 63 is set to a gain G3 for changing the amplitude of the original third canceling signal Sco3 shifted in phase by the phase shifter 53 so that it will become substantially equal to the amplitude of the road noise 2 at the position of the microphone 16.

Each of the second and fourth active noise controllers 12, 14 comprises a circuit based on a feed-forward filtered-X LMS algorithm.

The second active noise controller 12 includes a rotational frequency detector (fe1 detector) 72 comprising a frequency counter or the like for detecting a rotational frequency fe1 of an engine crankshaft (rotational member) from an engine rotation signal (engine pulses) supplied from a fuel injection ECU (FIECU), not shown, a second base signal generator (Sr2 generator) 22 for generating a second base signal S2 {cosine signal cos(2πfe1*t*) and sine signal sin(2πfe1t)} having a frequency equal to the rotational frequency fe1, a second adaptive filter 32 (second adaptive notch filter) for adjusting the phase and amplitude of the second base signal Sr2 to generate a second canceling signal Sc2, a reference signal generator (filter) 52 for filtering the second base signal Sr2 to generate a second reference signal r2, the reference signal generator 52 being set to simulative transfer characteristics C" and the like which simulate the transfer characteristics of the sound having the rotational frequency fe1 (each rotational frequency fe1 as it varies depending on the engine rotation signal) from an output terminal of the second active noise controller 12 for outputting the second canceling signal Sc2 through the mixer 20, the D/A converter 26, the speaker 28, the passenger compartment space 18 (sound field), the microphone 16, and the A/D converter 30 to an input terminal of the second active noise controller 12, i.e., an input terminal of a filter coefficient updater 42 to be described below, and a filter coefficient updater (algorithm processor) 42 for being supplied with the second reference signal r2 and the error signal e and updating a filter coefficient W2 (real part+i imaginary part=Rw2+iIw2) of the second adaptive filter 32 based on an adaptive control algorithm for minimizing the error signal e, e.g., an LMS algorithm which is one type of steepest descent method.

The noise to be canceled by a canceling sound based on the second canceling signal Sc2 is the muffled engine sound 1 which corresponds to the rotational frequency fe1 of the engine crankshaft.

The fourth active noise controller 14 includes a rotational frequency detector (fe2 detector) 74 comprising a frequency counter or the like for detecting a rotational frequency fe2 which is a harmonic of the rotational frequency of a propeller shaft (rotational member) from a vehicle speed signal (vehicle speed pulses) supplied from a vehicle speed sensor disposed near a countershaft, not shown, a fourth base signal generator (Sr4 generator) 24 for generating a fourth base signal S4 {cosine signal $\cos(2\pi fe2t)$ and sine signal $\sin(2\pi fe2t)$} having a frequency equal to the rotational frequency fe2, a fourth adaptive filter 34 (fourth adaptive notch filter) for adjusting the phase and amplitude of the fourth base signal Sr4 to generate a fourth canceling signal Sc4, a reference signal generator (filter) 54 for filtering the fourth base signal Sr4 to generate a fourth reference signal r4, the reference signal generator 54 being set to simulative transfer characteristics C^ which simulate the transfer characteristics of the sound having the rotational frequency fe2 (each rotational frequency fe2 as it varies depending on the rotational frequency of the propeller shaft) from an output terminal of the fourth active noise controller 14 for outputting the fourth canceling signal Sc4 through the mixer 20, the D/A converter 26, the speaker 28, the passenger compartment space 18 (sound field), the microphone 16, and the A/D converter 30 to an input terminal of the fourth active noise controller 14, i.e., an input terminal of a filter coefficient updater 44 to be described below, and a filter coefficient updater (algorithm processor) 44 for being supplied with the fourth reference signal r4 and the error signal e and updating a filter coefficient W4 (real part+i imaginary part=Rw4+iIw4) of the fourth adaptive filter 34 based on an adaptive control algorithm for minimizing the error signal e, e.g., an LMS algorithm which is one type of steepest descent method.

The noise to be canceled by a canceling sound based on the fourth canceling signal Sc4 is the muffled propeller shaft sound 2 which corresponds to the rotational frequency of the propeller shaft.

The amplitude suppressor 50 of the active noise control apparatus 10 monitors the amplitudes A1, A2, A3, A4 of the first, second, third, and fourth canceling signals Sc1, Sc2, Sc3, Sc4 based on the respective filter coefficients W1, W2, W3, W4, and adjusts the assignment of the output range DR of the mixer 20 based on the filter coefficients W1, W2, W3, W4 thereby to suppress the amplitudes A1, A2, A3, A4 of the first, second, third, and fourth canceling signals Sc1, Sc2, Sc3, Sc4.

The first active noise controller 11 shown in FIG. 1 which generates the canceling sound to cancel the road noise 1 having the frequency f1 may be replaced with an active noise controller according to the so-called adaptive feed-forward technology, i.e., the circuit technology based on the feed-forward filtered-X LMS algorithm, which detects a base signal with respect to suspension vibrations with a vibration detector, outputs the detected base signal as a canceling sound from the speaker 28 through an adaptive filter, detects a remaining noise generated by the interference between the canceling sound and the road noise 1, as an error signal with the microphone 16, inputs a reference signal generated based on acoustic transfer characteristics (simulative transfer characteristics from the speaker to the microphone) from the base signal and the error signal, and updates the filter coefficient of the adaptive filter in order to minimize the error signal.

FIG. 2 shows a noise reduction priority sequence table 40 for the first through fourth active noise controllers 11 through 14 of the active noise control apparatus 10 according to the embodiment. The noise reduction priority sequence table 40 is set or stored in a memory of the amplitude suppressor 50.

According to the present embodiment, a priority level 1 in the noise reduction priority sequence table 40 is set in the first active noise controller 11 which outputs the first canceling signal Sc1 for canceling the road noise 1 whose amplitude is most difficult to predict in advance. A priority level 2 is set in the third active noise controller 13 which outputs the third canceling signal Sc3 for canceling the road noise 2. A priority level 3 is set in the second active noise controller 12 which outputs the second canceling signal Sc2 for canceling the muffled engine sound 1. A priority level 4 is set in the fourth active noise controller 14 which outputs the fourth canceling signal Sc4 for canceling the muffled propeller shaft sound 2.

The active noise control apparatus 10 according to the present embodiment is basically constructed as described above. Operation of the active noise control apparatus 10 will be described below.

[Overall Operation]

Figure 3:
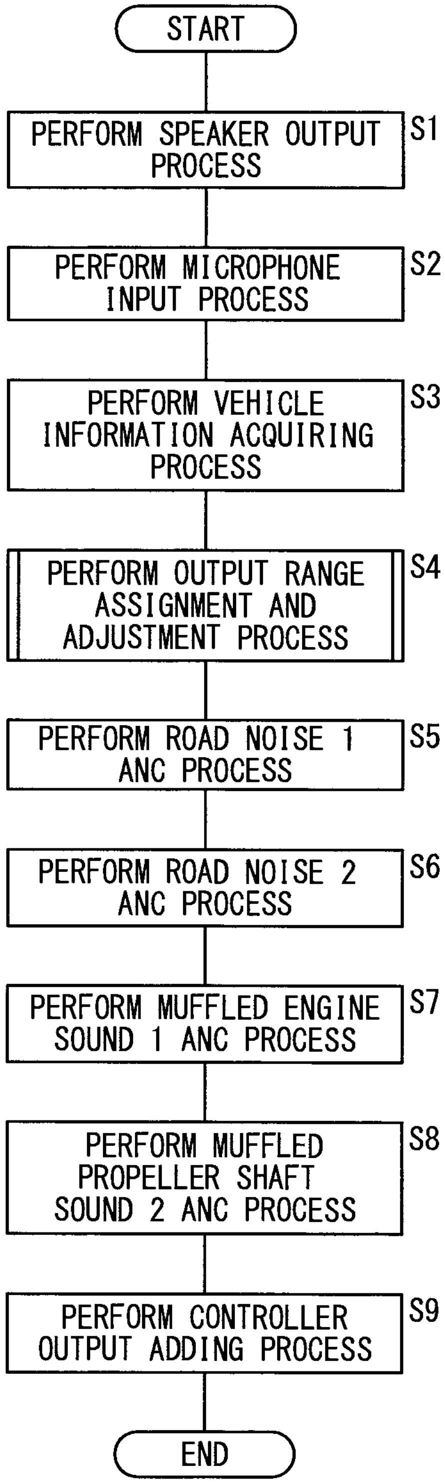
FIG. 3 is a flowchart of an operation sequence of the active noise control apparatus according to the embodiment.

FIG. 3 is a flowchart of the entire operation sequence of the active noise control apparatus 10 according to the embodiment. The operation sequence shown in FIG. 3 is carried out as an interrupt routine in constant cyclic periods by the amplitude suppressor 50 and the first through fourth active noise controllers 11 through 14.

In step S1, a speaker output process is performed in which the speaker 28 outputs canceling sounds for canceling the road noise 1, the road noise 2, the muffled engine sound 1, and the muffled propeller shaft sound 2 into the passenger compartment space 18 based on the first through fourth canceling sounds Sc1 through Sc4 that are generated by the first through fourth active noise controllers 11 through 14.

In step S2, a microphone input process is performed in which the microphone 16 detects a remaining noise generated by the interference between the road noise 1, the road noise 2, the muffled engine sound 1, and the muffled propeller shaft sound 2 and the canceling sounds therefor as an error signal e at the evaluating point, and outputs the error signal e to the first through fourth active noise controllers 11 through 14.

In step S3, a vehicle information acquiring process is performed in which vehicle information such as engine pulses and vehicle speed pulses is supplied to the second and fourth active noise controllers 12, 14.

In step S4, an assignment and adjustment process for the output range DR of the mixer 20 according to a first or second example is carried out as described in detail later.

Based on the results of the assignment and adjustment process for the output range DR of the mixer 20, filter coefficients W1 through S4 are established respectively for the first through fourth active noise controllers 11 through 14, and first through fourth canceling sounds Sc1 through Sc4 are generated respectively by the first through fourth active noise controllers 11 through 14 in steps S5 through S8 {in the flowchart shown in FIG. 3, a road noise 1 ANC (Active Noise Control) process in step S5, a road noise 2 ANC process in step S6, a muffled engine sound 1 ANC process in step S7, and a muffled propeller shaft sound 2 ANC process in step S8}.

In step S9, a controller output adding process is performed in which the first through fourth canceling sounds Sc1 through Sc4 that are generated respectively by the first through fourth active noise controllers 11 through 14 are mixed or added into a mixed canceling signal sc0 by the mixer 20. Then, control goes back to step S1.

[Operation of First Example]

Figure 4:
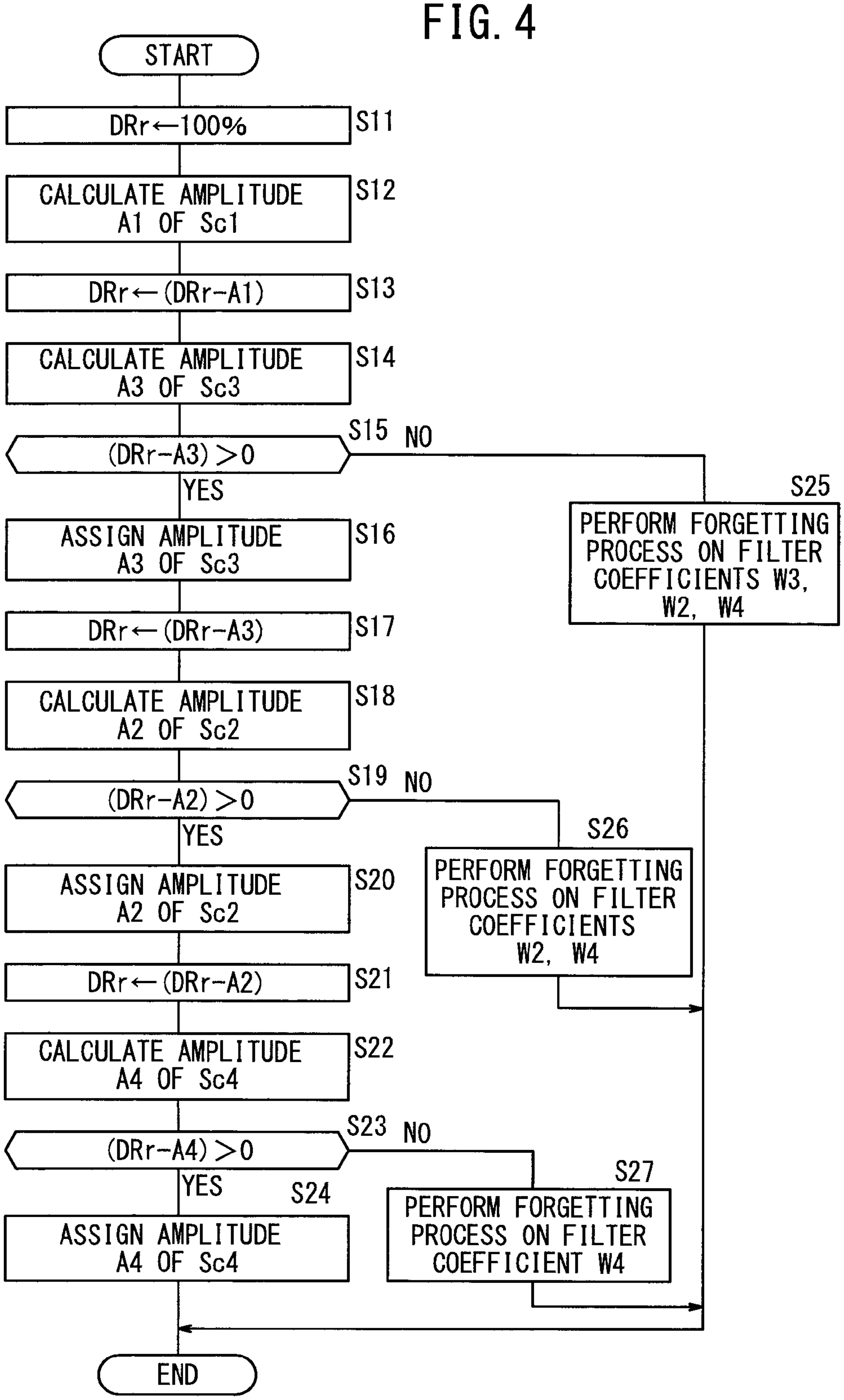
FIG. 4 is a flowchart showing details of an assignment and adjustment process for an output range according to a first example, which is carried out by an amplitude suppressor.

FIG. 4 is a flowchart showing details of an assignment and adjustment process for the output range DR of the mixer 20 according to a first example, which is carried out by the amplitude suppressor 50 in step S4.

In step S11 shown in FIG. 4, the amplitude suppressor 50 initializes a remaining output range DRr which represents a remainder of the output range DR (DRr←100 [%]).

In step S12, the amplitude suppressor 50 calculates an amplitude (amplitude demand value) A1 of the first canceling signal Sc1 at the priority level 1 based on a present filter coefficient W1 of the first adaptive filter 31 according to a following equation (1), and assigns the calculated amplitude A1 to the remaining output range DRr:

$$A1=G1\times\sqrt{\{(Rw1)^2+(Iw1)^2\}} \quad (1)$$

On the right side of the equation (1), G1 represents the gain of the gain setter 61 and $\sqrt{\{(Rw1)^2+(Iw1)^2\}}$ the magnitude of the filter coefficient W1 (W1=Rw1+i·Iw1) of the first adaptive filter 31.

In step S13, the amplitude suppressor 50 updates the remaining output range DRr according to a following expression (2):

$$DRr\leftarrow(DRr-A1) \quad (2)$$

In other words, the amplitude A1 is subtracted from the present remaining output range DRr to produce an updated remaining output range DRr.

In step S14, the amplitude suppressor 50 calculates an amplitude (amplitude demand value) A3 of the third canceling signal Sc3 at the priority level 2 based on a present filter coefficient W3 of the third adaptive filter 33 according to a following equation (3):

$$A3=G3\times\sqrt{\{(Rw3)^2+(Iw3)^2\}} \quad (3)$$

On the right side of the equation (3), G3 represents the gain of the gain setter 63 and $\sqrt{\{(Rw3)^2+(Iw3)^2\}}$ the magnitude of the filter coefficient W3 (W3=Rw3+i·Iw3) of the third adaptive filter 33.

In step S15, the amplitude suppressor 50 judges whether any remaining output range DRr of the mixer 20 is left or not according to a following inequality (4):

$$(DRr-A3)>0 \quad (4)$$

If there is left a remaining output range DRr, then the amplitude suppressor 50 assigns the amplitude A3 of the third canceling signal Sc3 to the remaining output range DRr of the mixer 20 in step S16. In step S17, the amplitude suppressor 50 updates the remaining output range DRr according to a following expression (5):

$$DRr\leftarrow(DRr-A3) \quad (5)$$

In step S18, the amplitude suppressor 50 calculates an amplitude (amplitude demand value) A2 of the second canceling signal Sc2 at the priority level 3 based on a present filter coefficient W2 of the second adaptive filter 32 according to a following equation (6):

$$A2=\sqrt{\{(Rw2)^2+(Iw2)^2\}} \quad (6)$$

On the right side of the equation (6), $\sqrt{\{(Rw2)^2+(Iw2)^2\}}$ represents the magnitude of the filter coefficient W2 (W2=Rw2+i·Iw2) of the second adaptive filter 32.

In step S19, the amplitude suppressor 50 judges whether any remaining output range DRr of the mixer 20 is left or not according to a following inequality (7):

$$(DRr-A2)>0 \quad (7)$$

If there is left a remaining output range DRr, then the amplitude suppressor 50 assigns the amplitude A2 of the second canceling signal Sc2 to the remaining output range DRr of the mixer 20 in step S20. In step S21, the amplitude suppressor 50 updates the remaining output range DRr according to a following expression (8):

$$DRr\leftarrow(DRr-A2) \quad (8)$$

In step S22, the amplitude suppressor 50 calculates an amplitude (amplitude demand value) A4 of the fourth canceling signal Sc4 at the priority level 4 based on a present filter coefficient W4 of the fourth adaptive filter 34 according to a following equation (9):

$$A4=\sqrt{\{(Rw4)^2+(Iw4)^2\}} \quad (9)$$

On the right side of the equation (9), $\sqrt{\{(Rw4)^2+(Iw4)^2\}}$ represents the magnitude of the filter coefficient W4 (W4=Rw4+i·Iw4) of the fourth adaptive filter 34.

In step S23, the amplitude suppressor 50 judges whether any remaining output range DRr of the mixer 20 is left or not according to a following inequality (10):

$$(DRr-A4)>0 \quad (10)$$

If there is left a remaining output range DRr, then the amplitude suppressor 50 assigns the amplitude A4 of the fourth canceling signal Sc4 to the remaining output range DRr of the mixer 20 in step S24. Thereafter, the assignment and adjustment process shown in FIG. 4 is ended. After steps S5 through S9 and steps S1 through S3 shown in FIG. 3 are performed, steps S11 through S24 shown in FIG. 4, which represent a subroutine of step S4, are repeated.

If it is judged in step S15 that the amplitude A3, calculated in step S14, of the third canceling signal Sc3 for canceling the road noise 2 at the priority level 2 cannot be assigned $\{(DRr-A3)\leq 0\}$, then a forgetting process is carried out for the filter coefficients W3, W2, W4 at the priority levels 2, 3, 4 in step S25. Specifically, a forgetting process is carried out to fade out the third, second, and fourth canceling signals Sc3, Sc2, Sc4 which generate canceling sounds using corrected filter coefficients that are produced by multiplying the filter coefficients W3, W2, W4 of the third, second, and fourth adaptive filters 33, 32, 34 of the third, second, and fourth active noise controllers 13, 12, 14, by a certain value smaller than 1, e.g., 127/128≈0.99.

Similarly, if it is judged in step S19 that the amplitude A2, calculated in step S18, of the second canceling signal Sc2 for canceling the muffled engine sound 1 at the priority level 3 cannot be assigned $\{(DRr-A2)\leq 0\}$, then a forgetting process is carried out for the filter coefficients W2, W4 (which have not been updated yet) at the priority levels 3, 4 in step S26. Specifically, a forgetting process is carried out to fade out the second and fourth canceling signals Sc2, Sc4 which generate canceling sounds using corrected filter coefficients that are produced by multiplying the filter coefficients W2, W4 of the second and fourth adaptive filters 32, 34 of the second and fourth active noise controllers 12, 14, by a certain value smaller than 1, e.g., 127/128≈0.99.

If it is judged in step S23 that the amplitude A4, calculated in step S22, of the fourth canceling signal Sc4 for canceling the muffled propeller shaft sound 2 at the priority level 4 cannot be assigned {(DRr−A4)≤0}, then a forgetting process is carried out for the filter coefficient W4 at the priority level 4 in step S27. Specifically, a forgetting process is carried out to fade out the fourth canceling signal Sc4 which generates a canceling sound using a corrected filter coefficient that is produced by multiplying the filter coefficient W4 (which has not been updated yet) of the fourth adaptive filter 34 of the fourth active noise controller 14, by a certain value smaller than 1, e.g., 127/128≈0.99.

Figure 5A:
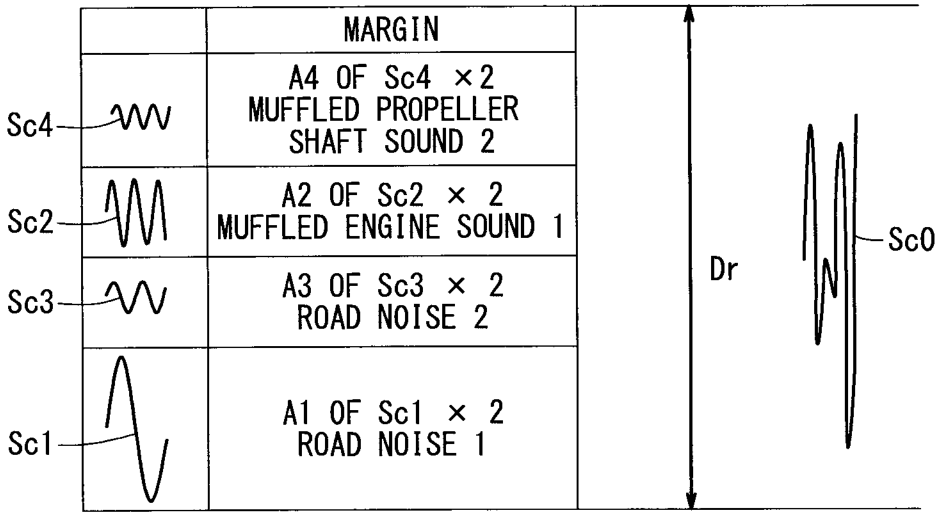
FIGS. 5A and 5B are diagrams showing how the first example operates and is advantageous.
Figure 5B:
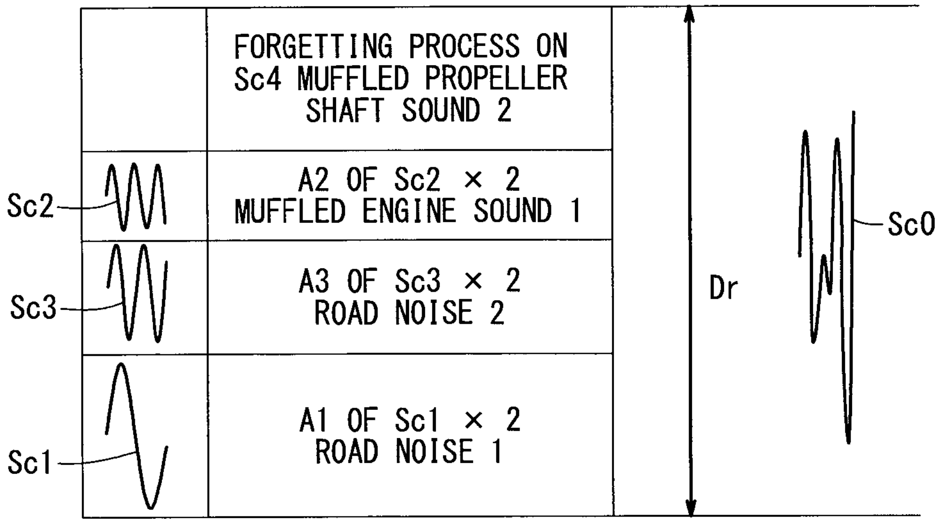
Figure 6A:
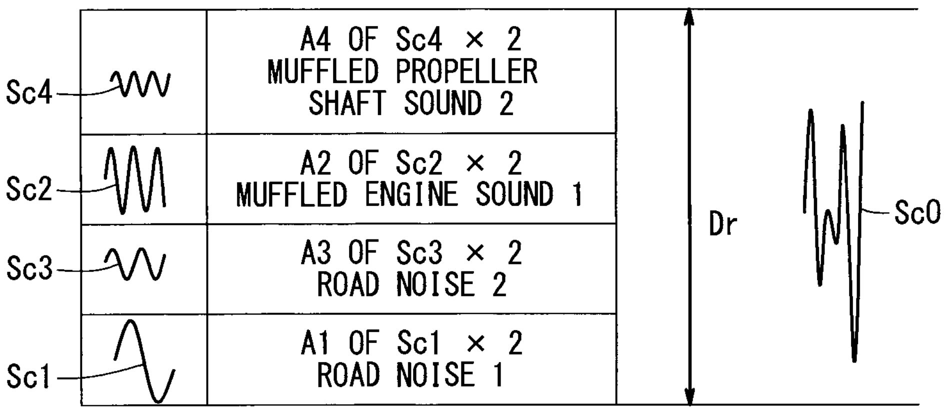
FIG. 6A Prior Art
FIGS. 6A and 6B are diagrams showing how an active noise control apparatus according to the related art operates.
Figure 6B:
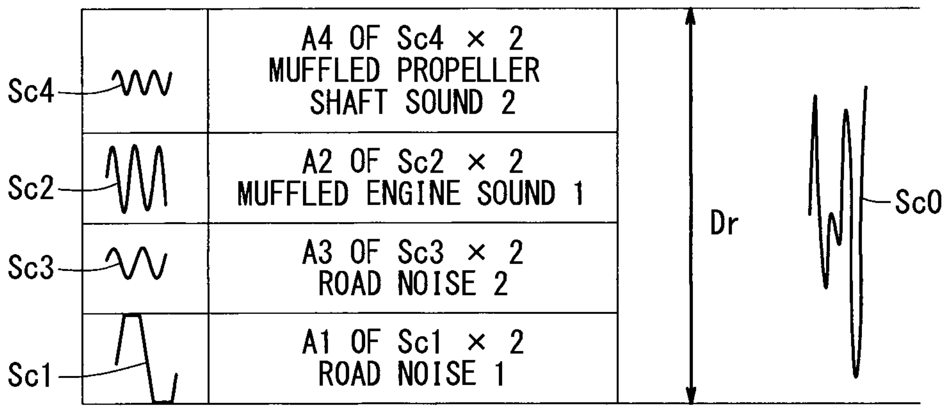
FIG. 6B Prior Art

FIGS. 5A and 5B are diagrams showing how the first example operates and is advantageous, and FIGS. 6A and 6B are diagrams showing how an active noise control apparatus according to the related art operates.

According to the first example, as shown in FIG. 5A, if the sum 2×(A1+A3+A2+A4) of the full amplitudes A1×2, A3×2, A2×2, A4×2 of the first, third, second, and fourth canceling signals Sc1, Sc3, Sc2, Sc4 is smaller than the output range DR, then since any one of the first, third, second, and fourth canceling signals Sc1, Sc3, Sc2, Sc4 is not clipped, the mixed canceling signal Sc0 output from the mixer 20 is supplied while undistorted through the D/A converter 26 to the speaker 28, which then output corresponding canceling sounds.

According to the first example, as shown in FIG. 5B, if the sum 2×(A1+A3+A2) of the full amplitudes A1×2, A3×2, A2×2 of the first, third, and second canceling signals Sc1, Sc3, Sc2 is smaller than the output range DR (step S19: YES), then any one of the first, third, and second canceling signals Sc1, Sc3, Sc2 is not clipped, but output as a canceling sound. If the answer to step S23 is negative {(DRr−A4)≤0}, then since a forgetting process is performed on the fourth canceling signal Sc4, the mixed canceling signal Sc0 that is output from the mixer 20 from the first, third, and second canceling signals Sc1, Sc3, Sc2 is not distorted.

According to the related art, as shown in FIG. 6A, if each of the full amplitudes A1×2, A3×2, A2×2, A4×2 of the first, third, second, and fourth canceling signals Sc1, Sc3, Sc2, Sc4 is smaller than ¼ of the output range DR, then since any one of the first, third, second, and fourth canceling signals Sc1, Sc3, Sc2, Sc4 is not clipped, the mixed canceling signal Sc0 is not distorted.

According to the related art, however, as shown in FIG. 6B, if either one of the full amplitudes A1×2, A3×2, A2×2, A4×2 of the first, third, second, and fourth canceling signals Sc1, Sc3, Sc2, Sc4, i.e., the full amplitude A1×2 of the first canceling signal Sc1 in this example, is greater than ¼ of the output range DR, then since the first canceling signal Sc1 is clipped, the mixed canceling signal Sc0 is distorted.

[Operation of Second Example]

Figure 7:
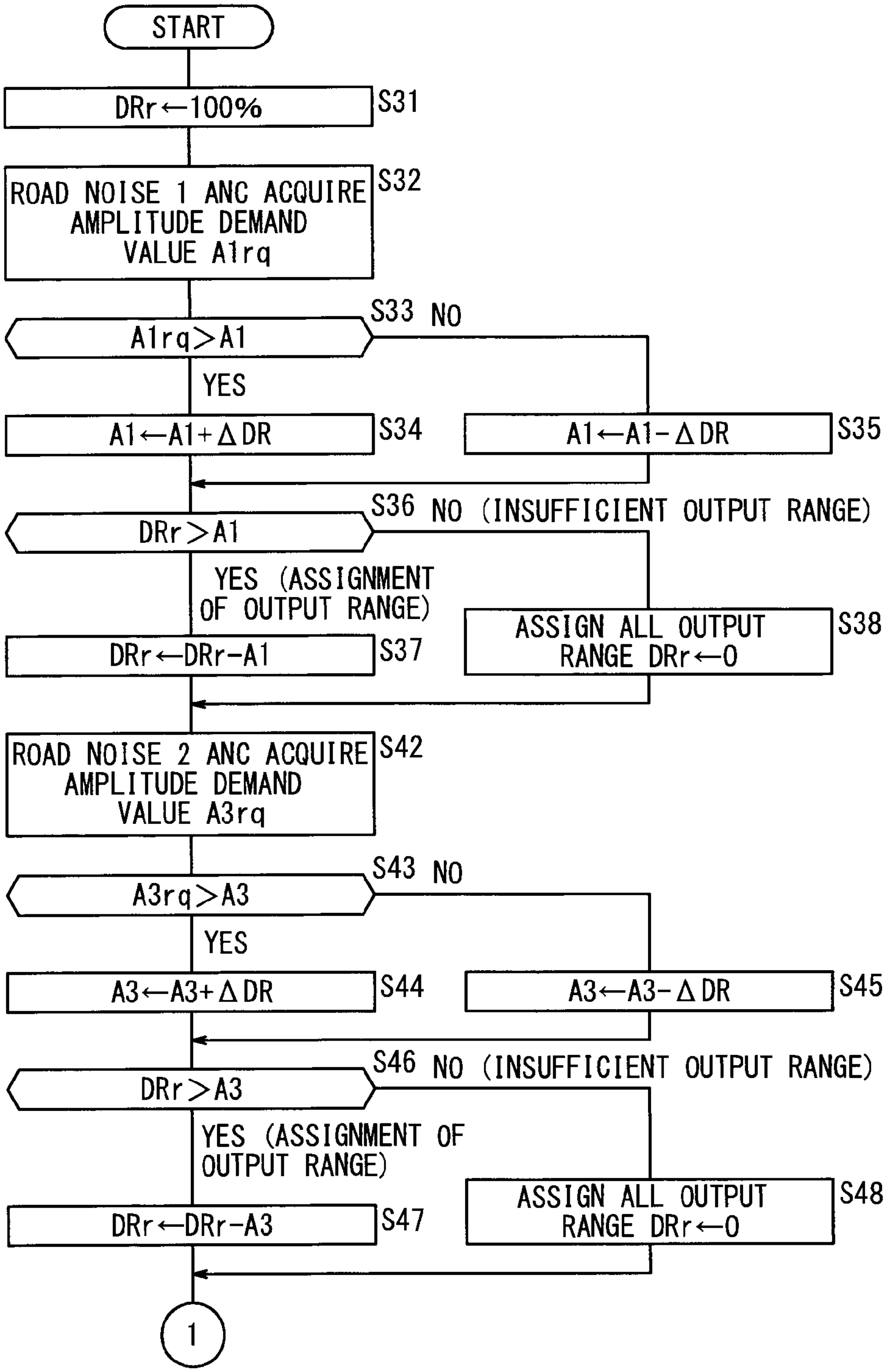
FIG. 7 is a flowchart (part 1) showing details of a process of assigning and adjusting output ranges according to a second example, which is carried out by the amplitude suppressor.
Figure 8:
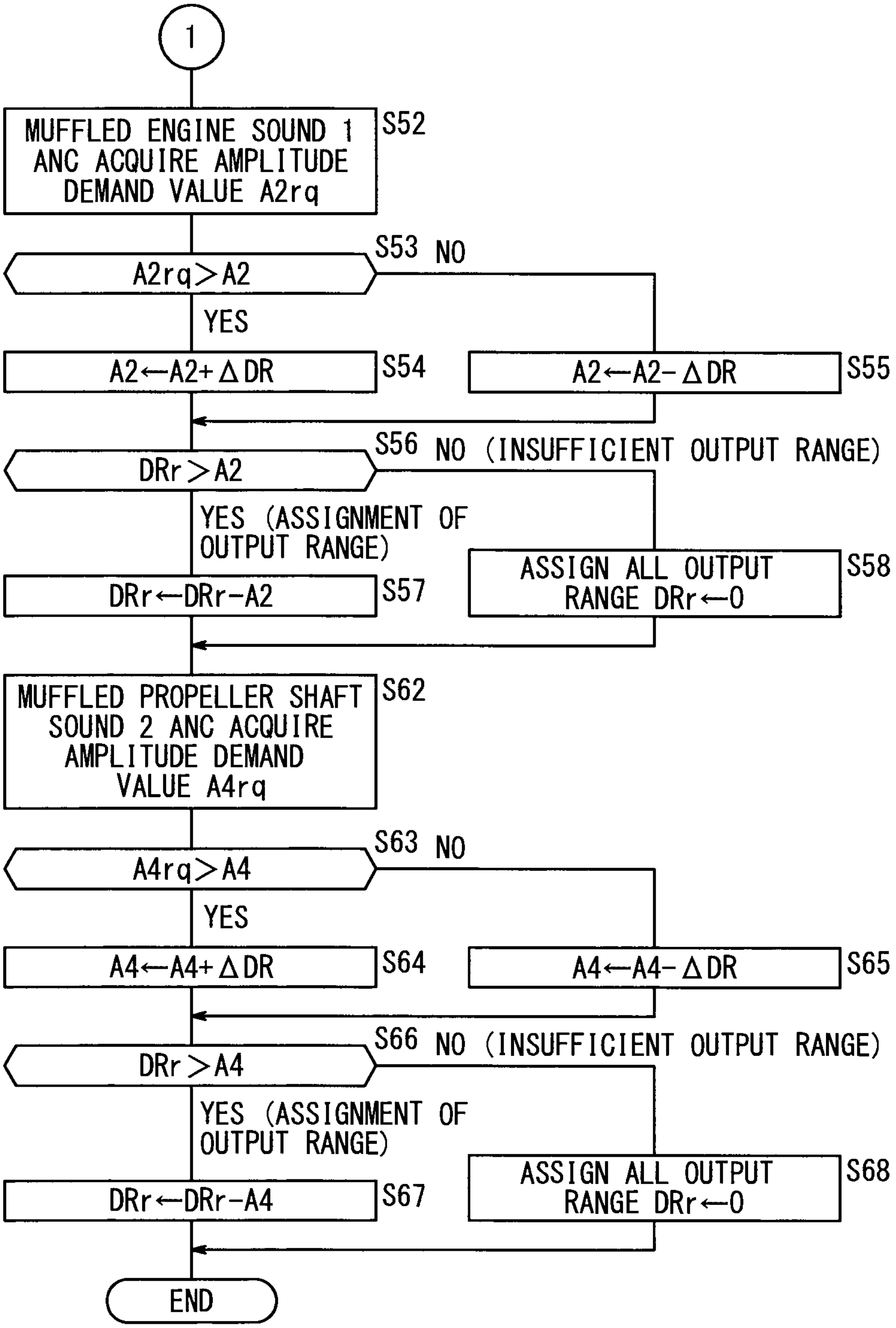
FIG. 8 is a flowchart (part 2) showing details of the process of assigning and adjusting output ranges according to the second example, which is carried out by the amplitude suppressor.

FIGS. 7 and 8 are flowcharts showing details of an assignment and adjustment process for the output range DR of the mixer 20 according to a second example, which is carried out by the amplitude suppressor 50 in step S4. The same or presumable operation in the second example as or from the operation in the first example will be omitted or described briefly for avoiding complexity.

In step S31 shown in FIG. 7, the amplitude suppressor 50 initializes a remaining output range DRr which represents a remainder of the output range DR (DRr←100 [%]).

In step S32, the amplitude suppressor 50 calculates an amplitude demand value A1$rq$ of the first canceling signal Sc1 at the priority level 1 based on a present filter coefficient W1 of the first adaptive filter 31 according to a following equation (11):

$$A1rq=K1\times G1\times\sqrt{\{(Rw1)^2+(Iw1)^2\}} \tag{11}$$

where K1 represents a margin coefficient which is preset to a certain value in the range of 2>K1>1. The margin coefficient K1 is set to a value greater than 1 in order to maintain the output range DR in a next updating cycle to allow the next updating cycle to a certain extent.

In step S33, the amplitude suppressor 50 judges whether or not the amplitude demand value A1$rq$ is greater than a present suppressed amplitude value A1[A1=G1×√{(Rw1)$^2$+(Iw1)$^2$}] that is calculated based on the filter coefficient W1 of the first adaptive filter 31.

If the amplitude suppressor 50 decides that the amplitude demand value A1$rq$ is greater than the present suppressed amplitude value A1 (step S33: YES), then the amplitude suppressor 50 performs a follow-up process for gradually increasing a target value to update the suppressed amplitude value A1 according to a following expression (12) in step S34:

$$A1\leftarrow(A1+\Delta DR) \tag{12}$$

where ΔDR represents a fixed value to be added to slightly increase the suppressed amplitude value A1 for the assignment of the output range DR.

If the amplitude suppressor 50 decides that the amplitude demand value A1$rq$ is not greater than the present suppressed amplitude value A1 (step S33: NO), then the amplitude suppressor 50 performs a follow-up process for gradually decreasing a target value to update the suppressed amplitude value A1 according to a following expression (13) in step S35:

$$A1\leftarrow(A1-\Delta DR) \tag{13}$$

In step S36, the amplitude suppressor 50 judges whether the updated suppressed amplitude value A1 is smaller than a remaining output range DRr or not.

If the updated suppressed amplitude value A1 is smaller than the remaining output range DRr (step S36: YES), then the amplitude suppressor 50 sets 1/G1 of the updated suppressed amplitude value A1 to the filter coefficient W1 of the first adaptive filter 31 of the first active noise controller 11 for silencing the road noise 1, and updates the remaining output range DRr according to a following expression (14) in step S37:

$$DRr\leftarrow(DRr-A1) \tag{14}$$

If the updated suppressed amplitude value A1 is not smaller than the remaining output range DRr (step S36: NO, DRr≤A1), then since the output range DR is insufficient, the amplitude suppressor 50 assigns all the output range DR of the mixer 20 to the first active noise controller 11 for silencing the road noise 1, and sets the remaining output range DRr to zero (DRr←0) in step S38.

Then, in step S42, the amplitude suppressor 50 calculates an amplitude demand value A3$rq$ of the third canceling signal Sc3 at the priority level 2 based on a present filter coefficient W3 of the third adaptive filter 33 according to a following equation (15):

$$A3rq=K3\times G3\times\sqrt{\{(Rw3)^2+(Iw3)^2\}} \tag{15}$$

where K3 represents a margin coefficient which is preset to a certain value in the range of 2>K3>1.

The processing of each of steps S43 through S48 is similar to the processing of each of steps S33 through S38, and will briefly be described below.

In step S43, the amplitude suppressor 50 judges whether or not the amplitude demand value A3$rq$ is greater than a present suppressed amplitude value A3 [A3=G3×√{(Rw3)$^2$+(Iw3)$^2$}] based on the filter coefficient W3 of the third adaptive filter 33. If the amplitude suppressor 50 decides that the amplitude demand value A3$rq$ is greater than the present suppressed amplitude value A3 (step S43: YES), then the amplitude suppressor 50 performs a follow-up process for gradually increasing a target value to update the suppressed amplitude value A3 according to a following expression (16) in step S44:

$$A3 \leftarrow (A3+\Delta DR) \quad (16)$$

If the amplitude suppressor 50 decides that the amplitude demand value A3*rq* is not greater than the present suppressed amplitude value A3 (step S43: NO), then the amplitude suppressor 50 performs a follow-up process for gradually decreasing a target value to update the suppressed amplitude value A3 according to a following expression (17) in step S45:

$$A3 \leftarrow (A3-\Delta DR) \quad (17)$$

In step S46, the amplitude suppressor 50 judges whether the updated suppressed amplitude value A3 is smaller than the remaining output range DRr or not.

If the updated suppressed amplitude value A3 is smaller than the remaining output range DRr (step S46: YES), then the amplitude suppressor 50 sets 1/G3 of the updated suppressed amplitude value A3 to the filter coefficient W3 of the third adaptive filter 33 of the third active noise controller 13 for silencing the road noise 2, and updates the remaining output range DRr according to a following expression (18) in step S47:

$$DRr \leftarrow (DRr-A3) \quad (18)$$

If the updated suppressed amplitude value A3 is not smaller than the remaining output range DRr (step S46: NO, DRr≤A3), then since the output range DR is insufficient, the amplitude suppressor 50 assigns all the output range DR of the mixer 20 to the third active noise controller 13 for silencing the road noise 2, and sets the remaining output range DRr to zero (DRr←0) in step S48. If the remaining output range DRr has already been set to zero in step S38, then the filter coefficient W3 of the third adaptive filter 33 is set to zero according to a forgetting process.

Then, in step S52 shown in FIG. 8, the amplitude suppressor 50 calculates an amplitude demand value A2*rq* of the second canceling signal Sc2 at the priority level 3 based on a present filter coefficient W2 of the second adaptive filter 32 according to a following equation (19):

$$A2rq=K2\times\sqrt{\{(Rw2)^2+(Iw2)^2\}} \quad (19)$$

where K2 represents a margin coefficient which is preset to a certain value in the range of 2>K2>1.

The processing of each of steps S53 through S58 is similar to the processing of each of steps S33 through S38, and will briefly be described below.

In step S53, the amplitude suppressor 50 judges whether or not the amplitude demand value A2*rq* is greater than a present suppressed amplitude value A2 [$A2=\sqrt{\{(Rw2)^2+(Iw2)^2\}}$]. If the amplitude suppressor 50 decides that the amplitude demand value A2*rq* is greater than the present suppressed amplitude value A2 (step S53: YES), then the amplitude suppressor 50 performs a follow-up process for gradually increasing a target value to update the suppressed amplitude value A2 according to a following expression (20) in step S54:

$$A2 \leftarrow (A2+\Delta DR) \quad (20)$$

If the amplitude suppressor 50 decides that the amplitude demand value A2*rq* is not greater than the present suppressed amplitude value A2 (step S53: NO), then the amplitude suppressor 50 performs a follow-up process for gradually decreasing a target value to update the suppressed amplitude value A2 according to a following expression (21) in step S55:

$$A2 \leftarrow (A2-\Delta DR) \quad (21)$$

In step S56, the amplitude suppressor 50 judges whether the updated suppressed amplitude value A2 is smaller than the remaining output range DRr or not.

If the updated suppressed amplitude value A2 is smaller than the remaining output range DRr (step S56: YES), then the amplitude suppressor 50 sets the updated suppressed amplitude value A2 to the filter coefficient W2 of the second adaptive filter 32 of the second active noise controller 12 for silencing the muffled engine sound 1, and updates the remaining output range DRr according to a following expression (22) in step S57:

$$DRr \leftarrow (DRr-A2) \quad (22)$$

If the updated suppressed amplitude value A2 is not smaller than the remaining output range DRr (step S56: NO, DRr≤A2), then since the output range DR is insufficient, the amplitude suppressor 50 assigns all the output range DR of the mixer 20 to the second active noise controller 12 for silencing the muffled engine sound 1, and sets the remaining output range DRr to zero (DRr←0) in step S58.

If the remaining output range DRr has already been set to zero in step S38 or step S48, then the filter coefficient W2 of the second adaptive filter 32 is set to zero according to a forgetting process.

Then, in step S62, the amplitude suppressor 50 calculates an amplitude demand value A4*rq* of the fourth canceling signal Sc4 at the priority level 4 based on a present filter coefficient W4 of the fourth adaptive filter 34 according to a following equation (23):

$$A4rq=K4\times\sqrt{\{(Rw4)^2+(Iw4)^2\}} \quad (23)$$

where K4 represents a margin coefficient which is preset to a certain value in the range of 2>K4>1.

The processing of each of steps S63 through S68 is similar to the processing of each of steps S33 through S38, and will briefly be described below.

In step S63, the amplitude suppressor 50 judges whether or not the amplitude demand value A4*rq* is greater than a present suppressed amplitude value A4 [$A4=\sqrt{\{(Rw4)^2+(Iw4)^2\}}$]. If the amplitude suppressor 50 decides that the amplitude demand value A4*rq* is greater than the present suppressed amplitude value A4 (step S63: YES), then the amplitude suppressor 50 performs a follow-up process for gradually increasing a target value to update the suppressed amplitude value A4 according to a following expression (24) in step S64:

$$A4 \leftarrow (A4+\Delta DR) \quad (24)$$

If the amplitude suppressor 50 decides that the amplitude demand value A4*rq* is not greater than the present suppressed amplitude value A4 (step S63: NO), then the amplitude suppressor 50 performs a follow-up process for gradually decreasing a target value to update the suppressed amplitude value A4 according to a following expression (25) in step S65:

$$A4 \leftarrow (A4-\Delta DR) \quad (25)$$

In step S66, the amplitude suppressor 50 judges whether the updated suppressed amplitude value A4 is smaller than the remaining output range DRr or not.

If the updated suppressed amplitude value A4 is smaller than the remaining output range DRr (step S66: YES), then the amplitude suppressor 50 sets the updated suppressed amplitude value A4 to the filter coefficient W4 of the fourth adaptive filter 34 of the fourth active noise controller 14 for silencing the propeller shaft sound 2, and updates the remaining output range DRr according to a following expression (26) in step S67:

$$DRr \leftarrow (DRr - A4) \qquad (26)$$

If the updated suppressed amplitude value A4 is not smaller than the remaining output range DRr (step S66: NO, DRr≤A4), then since the output range DR is insufficient, the amplitude suppressor 50 assigns all the output range DR of the mixer 20 to the fourth active noise controller 14 for silencing the propeller shaft sound 2, and sets the remaining output range DRr to zero (DRr←0) in step S68.

If the remaining output range DRr has already been set to zero in step S38 or step S48 or step S58, then the filter coefficient W4 of the fourth adaptive filter 34 is set to zero according to a forgetting process.

[Summary of the Embodiment]

Figure 9:
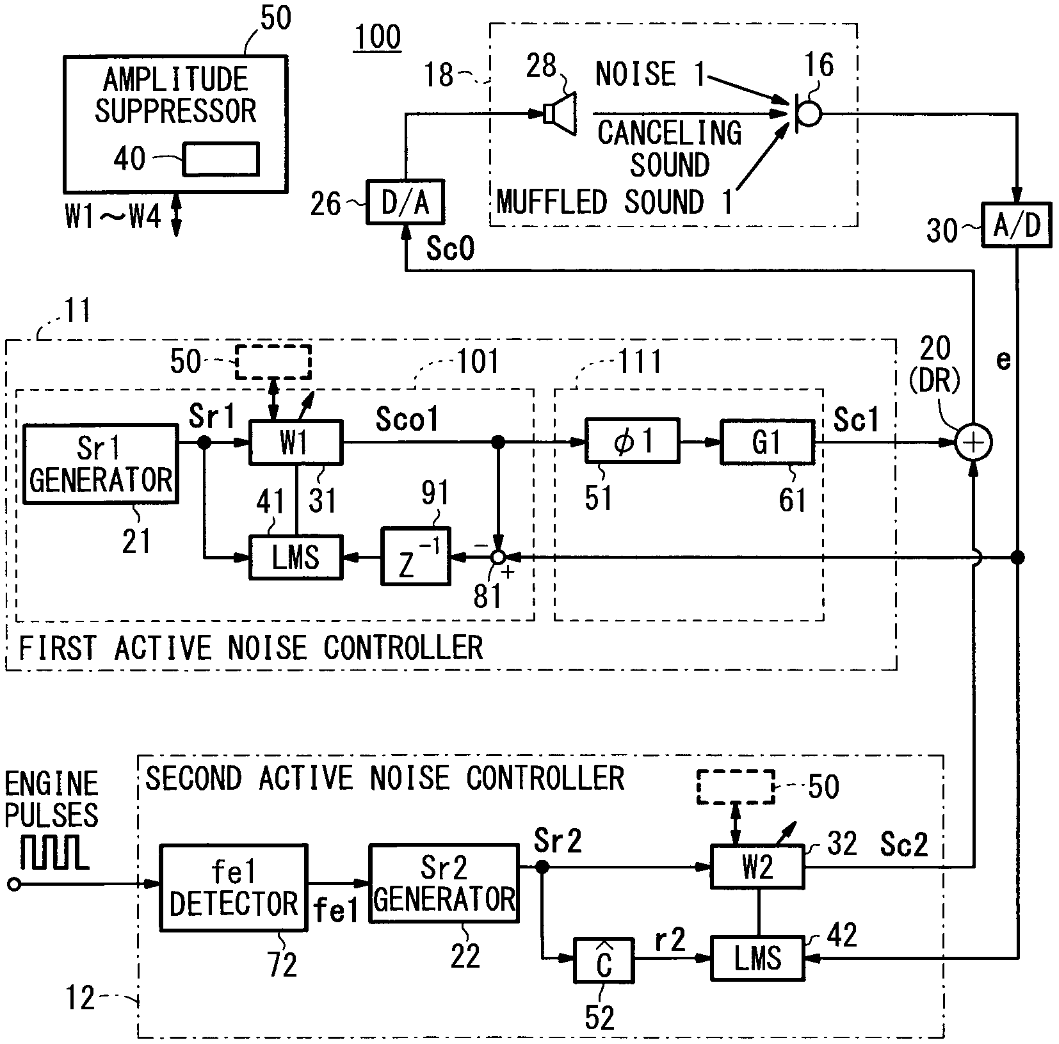
FIG. 9 is a block diagram of an active noise control apparatus illustrated for an easier understanding of the configuration of the active noise control apparatus according to the embodiment, including the first and second examples, and an easier understanding of how the active noise control apparatus according to the embodiment operates and is advantageous.

The configuration and advantages of the active noise control apparatus according to the present embodiment which includes the first and second examples described above will be described with respect to an active noise control apparatus 100 shown in FIG. 9 which includes two active noise controllers, i.e., a first active noise controller 11 for silencing the road noise 1 at the priority level 1 and a second active noise controller 12 for silencing the muffled engine sound 1 at the priority level 3 (priority level 2 in FIG. 9), for an easier understanding of the present invention.

The active noise control apparatus 100 includes a first active noise controller 11 which generates a first canceling signal Sc1 for a first noise type, a second active noise controller 12 which generates a second canceling signal Sc2 for a second noise type that is different from the first noise type, a mixer 20 for mixing the first canceling signal Sc1 and the second canceling signal Sc2 into a mixed canceling signal Sc0, a speaker 28 as a canceling sound output unit for outputting a canceling signal based on the mixed canceling signal Sc0, and an amplitude suppressor 50 for suppressing the amplitude A2 $[A2=\sqrt{\{(Rw2)^2+(Iw2)^2\}}]$ of the second canceling signal Sc2 depending on the amplitude A1 $[A1=G1\times\sqrt{\{(Rw1)^2+(Iw1)^2\}}]$ of the first canceling signal Sc1.

Since the active noise control apparatus 100 has the amplitude suppressor 50 that suppresses the amplitude A2 of the second canceling signal Sc2 which is input to the mixer 20 depending on the amplitude A1 of the first canceling signal Sc1 which is input to the mixer 20, the active noise control apparatus 100 is capable of outputting an optimum canceling sound depending on how a vehicle that incorporates the active noise control apparatus 100 travels, by optimizing the use of the output range DR (DR/2 if corresponding to the amplitude) of the mixer 20.

If the sum (A1+A2) of the amplitude A1 of the first canceling signal Sc1 and the amplitude A2 of the second canceling signal Sc2 is greater than the maximum output amplitude DR/2 allowed by the mixer 20 $\{(A1+A2)>(DR/2)\}$, then the amplitude suppressor 50 sets the amplitude A2 of the second canceling signal Sc2 to the difference that is produced when the amplitude A1 of the first canceling signal Sc1 is subtracted from the allowable maximum output amplitude DR/2 of the mixer 20 $[A2\le\{(DR/2)-A1\}]$, preventing the amplitude A1 of the first canceling signal Sc1 from being clipped as much as possible.

If the sum (A1+A2) of the amplitude A1 of the first canceling signal Sc1 and the amplitude A2 of the second canceling signal Sc2 is greater than the maximum output amplitude DR/2 allowed by the mixer 20 $\{(A1+A2)>(DR/2)\}$, then the amplitude suppressor 50 sets the amplitude A2 of the second canceling signal Sc2 to zero, also preventing the amplitude A1 of the first canceling signal Sc1 from being clipped as much as possible.

The first active noise controller 11 and the second active noise controller 12 have the first and second adaptive notch filters 101, 32, respectively (through the reference numeral 32 is described as representing an adaptive filter, it may also be considered as an adaptive notch filter because it adaptively attenuates the muffled engine sound 1 having the rotational frequency fe1), and the amplitude A1 $[A1=G1\times\sqrt{\{(Rw1)^2+(Iw1)^2\}}]$ of the first canceling signal Sc1 and the amplitude A2 $[A2=\sqrt{\{(Rw2)^2+(Iw2)^2\}}]$ of the second canceling signal Sc2 are calculated from the respective filter coefficients W1, W2 of the first and second adaptive notch filters 101, 32. Therefore, the amplitude A1 of the first canceling signal Sc1 and the amplitude A2 of the second canceling signal Sc2 can be calculated simply.

When the first noise type represents the road noise 1, even if the amplitude A1 of the first canceling signal Sc1 cannot be predicted beforehand, the desired first canceling signal Sc1 is prevented from being clipped, and the active noise control apparatus 100 is capable of outputting an optimum canceling sound depending on how a vehicle that incorporates the active noise control apparatus 100 travels, by optimizing the use of the output range DR of the mixer 20.

The active noise control apparatus 100 includes first and second active noise controllers 11, 12 which generate a plurality of first and second canceling signals Sc1, Sc2 respectively for a plurality of noise types, a mixer 20 for mixing the first and second canceling signals Sc1, Sc2 into a mixed canceling signal Sc0, a speaker 28 as a canceling sound output unit for outputting a canceling sound based on the mixed canceling signal Sc0, the noise types being in accordance with a noise reduction priority sequence (the priority level of the noise type to be canceled by the first active noise controller 11 is higher than the priority level of the noise type to be canceled by the second active noise controller 12) established therefor, and an amplitude suppressor 50 for suppressing the amplitude of at least one (whose priority level is lower) of the first and second canceling signals Sc1, Sc2, i.e., the amplitude A2 of the second canceling signal Sc2, depending on the noise reduction priority sequence.

Since the amplitude A2 of the second canceling signal Sc2, i.e., the amplitude of at least one of the canceling signals for canceling the noise type whose priority level is lower, is suppressed by the amplitude suppressor 50, the amplitude A1 of the first canceling signal Sc1 for canceling the noise type whose priority level is higher is prevented from being suppressed accordingly.

The present invention is not limited to the above embodiment, but may changes and modifications may be made based on the disclosure of the above description. For example, the active noise control apparatus 100 shown in FIG. 9 may be devoid of the second active noise controller 12 for canceling the muffled engine sound 1, but may instead include an active sound effect generation controller at the priority level 2 for generating a base signal based on a signal representing detected engine vibrations, generating a control signal by changing the amplitude and phase of the base signal to produce an acceleration-dependent sound effect, and supplying the control signal via the mixer 20 to the speaker 28 to produce a sound effect (accelerating sound) in the passenger compartment space 18, or the active noise control apparatus 10 shown in FIG. 1 may include such an active sound effect generation controller at a priority level 5.

What is claimed is:

1. An active noise control apparatus, comprising:

a first active noise controller for generating a first canceling signal for a first noise type, the first active noise controller including a first adaptive notch filter;

a second active noise controller for generating a second canceling signal for a second noise type that is different from the first noise type, the second active noise controller including a second adaptive notch filter;

a mixer for mixing the first canceling signal and the second canceling signal into a mixed canceling signal;

a canceling sound output unit for outputting a canceling sound based on the mixed canceling signal; and an amplitude suppressor for calculating an amplitude of the first canceling signal based on a filter coefficient of the first adaptive notch filter, calculating an amplitude of the second canceling signal based on a filter coefficient of the second adaptive notch filter, and suppressing the amplitude of the second canceling signal depending on the amplitude of the first canceling signal, wherein if the amplitude of the second canceling signal cannot be assigned within a value range which is produced when the amplitude of the first canceling signal is subtracted from a maximum output amplitude allowed by the mixer, the amplitude suppressor decreases the filter coefficient of the second adaptive notch filter to fade out the second canceling signal.

2. The active noise control apparatus according to claim 1, further comprising:

a plurality of active noise controllers, including the first active noise controller and the second active noise controller, for generating a plurality of canceling signals respectively for a plurality of noise types;

wherein the mixer mixes the canceling signals into a mixed canceling signal; and the amplitude suppressor suppresses an amplitude of at least one of the canceling signals depending on a noise reduction priority sequence preset for the noise types.

3. The active noise control apparatus according to claim 1, wherein if a sum of the amplitude of the first canceling signal and the amplitude of 1 the second canceling signal is greater than the maximum output amplitude allowed by the mixer, the amplitude suppressor sets the amplitude of the second canceling signal to a difference which is produced when the amplitude of the first canceling signal is subtracted from the maximum output amplitude allowed by the mixer.

4. The active noise control apparatus according to claim 1, wherein if the sum of the amplitude of the first canceling signal and the amplitude of the second canceling signal is greater than the maximum output amplitude allowed by the mixer, the amplitude suppressor sets the amplitude of the second canceling signal to zero.

5. The active noise control apparatus according to claim 1, wherein the first noise type represents a road noise.

6. The active noise control apparatus according to claim 2, wherein the noise reduction priority sequence has a succession of priority levels set respectively to a road noise which is caused by resonance of suspensions and has its magnitude that varies depending on conditions of a road, a drumming noise caused by resonance of a sound field in a passenger compartment, a muffled engine sound corresponding to a rotational frequency of an engine crankshaft, and a muffled propeller shaft sound corresponding to a rotational frequency of a propeller shaft.

7. The active noise control apparatus according to claim 2, wherein the amplitude suppressor updates a remaining output range of the mixer each time one of the amplitudes of the canceling signals generated respectively by the active noise controllers is assigned to the output range of the mixer in a descending order of the noise types according to the noise reduction priority sequence, and performs a forgetting process for fading out the amplitude of one of the canceling signals for the noise types which cannot be assigned within the remaining output range of the mixer.

* * * * *